(12) United States Patent
Isch et al.

(10) Patent No.: US 8,092,864 B2
(45) Date of Patent: Jan. 10, 2012

(54) MANDREL AND METHOD FOR COATING OPEN-CELL IMPLANTABLE ENDOVASCULAR STRUCTURES

(75) Inventors: Andrew P. Isch, Lafayette, IN (US); Jeff P. Little, Lafayette, IN (US); Patrick H. Ruane, San Mateo, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 805 days.

(21) Appl. No.: 12/199,189

(22) Filed: Aug. 27, 2008

(65) Prior Publication Data

US 2009/0061072 A1    Mar. 5, 2009

Related U.S. Application Data

(60) Provisional application No. 60/968,436, filed on Aug. 28, 2007.

(51) Int. Cl.
*B05D 3/00* (2006.01)
(52) U.S. Cl. ....... 427/335; 427/2.24; 427/2.28; 427/2.3; 427/2.31
(58) Field of Classification Search ................. 427/335, 427/2.24, 2.28, 2.3, 2.31
See application file for complete search history.

(56) References Cited

U.S. PATENT DOCUMENTS

| | | | |
|---|---|---|---|
| 4,739,762 A | 4/1988 | Palmaz | 128/343 |
| 5,133,732 A | 7/1992 | Wiktor | 606/195 |
| 5,292,331 A | 3/1994 | Boneau | 606/198 |
| 5,421,955 A | 6/1995 | Lau et al. | 216/48 |
| 6,090,127 A | 7/2000 | Globerman | 606/194 |
| 6,120,847 A * | 9/2000 | Yang et al. | 427/335 |
| 6,517,889 B1 | 2/2003 | Jayaraman | 427/2.24 |
| 6,565,659 B1 | 5/2003 | Pacetti et al. | 118/500 |
| 6,572,644 B1 | 6/2003 | Moein | 623/1.11 |
| 6,818,063 B1 | 11/2004 | Kerrigan | 118/500 |
| 6,955,723 B2 | 10/2005 | Pacetti et al. | 118/500 |
| 7,060,319 B2 | 6/2006 | Fredrickson | 427/2.24 |
| 7,306,677 B2 | 12/2007 | Robida | 118/503 |

(Continued)

FOREIGN PATENT DOCUMENTS

WO    WO 03/006180 A1    1/2003

*Primary Examiner* — Eisa Elhilo
(74) *Attorney, Agent, or Firm* — Brinks Hofer Gilson & Lione

(57) ABSTRACT

Methods of coating a medical device are provided to improve coating uniformity and reduce coating irregularities while reducing direct coating of the luminal surface of the medical device. Preferably, methods of coating a tubular medical device include the steps of: positioning the tubular medical device around a mandrel coating assembly, mounting the tubular medical device on the mandrel coating assembly and spraying a coating solution including a therapeutic agent and a solvent onto the abluminal surface of the tubular medical device mounted on the mandrel coating assembly. The mandrel coating assembly may include an axial member of a diameter that is less than the diameter of the lumen of the tubular medical device and at least one annular projection extending from the axial member to an outer surface having a diameter greater than or substantially equal to the diameter of the lumen of the medical device. Improved coating uniformity may be achieved by providing an annular space between the luminal surface of the medical device and an axial member. Coating on the luminal surface may be minimized by providing an axial member having an outer diameter that is greater than the maximum width or length of the spray contacting the axial member after passing through the openings in the medical device.

20 Claims, 6 Drawing Sheets

U.S. PATENT DOCUMENTS

| | | | |
|---|---|---|---|
| 7,354,480 B1 | 4/2008 | Kokish et al. | 118/500 |
| 7,402,329 B2 | 7/2008 | Pacetti et al. | 427/2.1 |
| 2004/0013792 A1 | 1/2004 | Epstein et al. | 427/2.24 |
| 2005/0069630 A1 | 3/2005 | Fox et al. | 427/2.24 |
| 2006/0035012 A1 | 2/2006 | Pacetti et al. | 427/2.1 |
| 2006/0284383 A1 | 12/2006 | Brettell | 279/2.1 |
| 2006/0286287 A1 | 12/2006 | Hossainy | 427/2.1 |
| 2007/0031611 A1 | 2/2007 | Babaev | 427/600 |
| 2007/0048433 A1 | 3/2007 | Hallett et al. | 427/2.1 |
| 2007/0048452 A1 | 3/2007 | Feng et al. | 427/458 |
| 2008/0124452 A1 | 5/2008 | Kokish et al. | 427/2.25 |

\* cited by examiner

MANDREL AND METHOD FOR COATING OPEN-CELL IMPLANTABLE ENDOVASCULAR STRUCTURES

CROSS-REFERENCE TO RELATED APPLICATIONS

This application is related to and claims priority to U.S. Provisional Patent Application Ser. No. 60/968,436, filed Aug. 28, 2007, which is incorporated by reference herein its entirety.

TECHNICAL FIELD

The present invention relates to methods of coating medical devices, such as open-celled endovascular stents, and mandrel assembly structures useful in performing said coating methods.

BACKGROUND

Coatings may be applied to medical devices to provide certain advantages or functionality. Medical devices may be coated so that the surfaces of such devices have desired properties or effects. For example, medical device coatings may provide localized delivery of therapeutic agents to target locations within the body, such as to treat localized disease (e.g., heart disease) or occluded body lumens. Localized drug delivery may mitigate undesirable side effects or costs of systemic drug administration. Additionally, localized delivery of a therapeutic agent from a coating may provide a higher concentration of therapeutic agent at a specific point of treatment than would otherwise be achievable by systemic administration. Localized drug delivery may be achieved, for example, by coating endovascular devices such as balloon catheters, stents and the like with the therapeutic agent to be locally delivered. The coating on medical devices may provide for controlled release, which may include long-term or sustained release, of a bioactive material.

For certain medical applications, a coating containing a therapeutic agent is applied to the external surface of an endovascular medical device. The medical device may be configured to bring the coating into therapeutically effective contact with the wall of a body vessel. For instance, the medical device may be a radially expandable tubular stent formed by a plurality of interconnected members defining open cells extending between an external (abluminal) surface and an internal (luminal) surface. A releasable therapeutic agent may be applied to the abluminal surface of the stent for delivery to a treatment site within a body vessel. The luminal surface defines a tubular lumen extending axially from the proximal end to the distal end of the stent. Such coated stent structures are commonly deployed within a body vessel to maintain patency of a stenosis, and the therapeutic agent may be selected to mitigate or prevent restenosis of the body vessel after dilation. For example, the stent may be delivered endovascularly using a catheter delivery system by expanding the stent from a radially compressed delivery configuration within a portion of the catheter to a radially expanded configuration within the body vessel. The stent delivery may be performed as part of a procedure to dilate a blood vessel with the catheter balloon, such as percutaneous transcoronary angioplasty (PCTA). The stent may be radially expanded by a balloon attached to the catheter or may be formed of a material that radially self-expands when released from the catheter.

For many such medical procedures, coated endolumenal devices are preferably coated on the abluminal surface with a particular therapeutic agent in a manner that provides a uniform coating and minimizes coating of the luminal surface. In addition, the therapeutic agent is preferably localized on the interconnected members (e.g., struts and bends) of the stent, rather than being present within the open cells between these members. Upon radial expansion of the endolumenal device, the distance between adjacent members typically increases and the area enclosed by the open cells between these members typically increases. As such, therapeutic agent coated over, or bridging, such open cells may fall through the cells, into the lumen and be undesirably washed away from the point of treatment without contacting the wall of the body vessel. Therefore, coating methods that localize application of the therapeutic agent to the desired coating surfaces of the endolumenal medical device are particularly desirable.

Coatings have been applied to medical devices by processes such as dipping, spraying, vapor deposition, plasma polymerization, and electrodeposition. Although these processes have been used to produce satisfactory coatings, they have numerous, associated, potential drawbacks. For example, it may be difficult to achieve coatings of uniform thicknesses, both on individual parts and on batches of parts. Also, these coating processes may require that the coated part be held during coating, which may result in defects such as bare spots where the part was held and which may thus require subsequent coating steps. Further, many conventional processes require multiple coating steps or stages for the application of a second coating material, or to allow for drying between coating steps or after the final coating step.

One method of coating an endoluminal medical device involves mounting the endoluminal medical device on a mandrel and spraying a solution of a therapeutic agent in a volatile solvent onto the abluminal surface of the mounted endoluminal medical device. The solvent is allowed to evaporate, leaving the abluminal surface coated with the therapeutic agent. Optionally, a polymer may be dissolved in the solution with the therapeutic agent and solvent, or applied with the solvent to form a separate coating layer from the therapeutic agent. When the endoluminal medical device is a tubular radially expandable structure, such as a stent, the medical device is typically mounted on the mandrel in a radially expanded position including a plurality of openings. One difficulty with the above-described method of coating the stent is the potential for coating defects. While some coating defects can be minimized by adjusting the coating parameters, other defects occur due to the nature of the interface between the stent and the mandrel on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus, also referred to as "webbing" of the coating. Upon the removal of the coated stent from the supporting apparatus, the excess webbed coating may stick to the apparatus, thereby removing some of the needed coating from the stent and leaving bare areas. Alternatively, the excess coating may stick to the stent, thereby leaving excess coating as clumps or pools on the struts or webbing between the struts. During implantation of the coated stent, excess therapeutic agent deposited within the openings in the stent frame may be dislodged upon radial expansion of the coated stent and fall through the openings into the lumen of the stent.

Thus, there is a need for coating methods and structures useful to minimize the interface between the stent and the apparatus supporting the stent during the coating process to minimize adverse coating defects. Accordingly, the present invention provides for a device for supporting a stent during the coating application process. The invention also provides for a method of coating the stent supported by the device.

SUMMARY

Methods of coating a medical device are provided to improve coating uniformity and reduce coating irregularities such as "webbing" without coating the luminal surface of the medical device. Preferably, methods of coating a tubular medical device include the steps of: positioning the tubular medical device around a mandrel coating assembly, mounting the tubular medical device on the mandrel coating assembly and spraying a coating solution including a therapeutic agent and a solvent onto the abluminal surface of the tubular medical device mounted on the mandrel coating assembly. The tubular medical device may extend along a longitudinal axis from a proximal end to a distal end and have a plurality of openings between an abluminal surface and a luminal surface defining a substantially cylindrical lumen having a first diameter. The mandrel coating assembly may include an axial member of a second diameter that is less than the first diameter of the lumen of the tubular medical device and at least one annular projection extending from the axial member to an outer surface having a diameter greater than or substantially equal to the first diameter. Preferably, the coating solution may be sprayed onto the mounted tubular medical device to coat the abluminal surface of the medical device with the therapeutic agent while a portion of the coating solution spray passes through at least one opening in the medical device in a spray pattern having a cross sectional area that is less than the cross sectional area of the axial member and terminates at the axial member. The coating solution spray can be applied without directly contacting the luminal surface of the medical device. Improved coating uniformity may be better achieved by providing a floating stent, i.e., an annular space between the luminal surface of the medical device and the axial member. Coating on the luminal surface may be minimized by providing an axial member having an outer diameter that is greater than the maximum width or length of the spray contacting the axial member after passing through the openings in the medical device.

In a first embodiment, the tubular medical device may be mounted on the mandrel coating assembly with a first portion of the luminal surface contacting the outer surface of the annular projection, with at least a second portion of the luminal surface spaced apart from and substantially parallel to the axial member.

In a second embodiment, the tubular medical device may be mounted on the mandrel coating assembly between two annular projections with a proximal end of the vascular device contacting the first annular projection and a distal end of the vascular device contacting the second annular projection, the vascular stent being secured to the mandrel coating assembly by contact with the first annular projection and the second annular projection with the luminal surface spaced apart from and substantially parallel to the axial member. Each annular projection can have an annular groove sized to receive the respective proximal and distal ends of the tubular medical device. The annular groove can be on one side or both sides of each annular projection, and can be two different diameters on either side of the annular projection.

In a third embodiment, the mandrel coating assembly can be broken down into components, which can permit easier loading of the medical device onto the mandrel coating assembly. The mandrel coating assembly can have a first axial member component and a second axial member component, each having a second diameter that is less than the first diameter of the lumen of the tubular medical device. The first and second axial member components can be removably coupled to one another. Each axial member component can have an annular projection and a means for coupling to another axial member component. Each annular projection can extend from the respective axial member component to an outer surface having a diameter greater than the first diameter. The tubular medical device can be mounted on one of the axial member components with the proximal end of the tubular medical device contacting the annular projection. Each of the axial member components can be coupled to one another by the means for coupling where a portion of the tubular medical device contacts the annular projection of each axial member. The tubular medical device can be secured to the mandrel coating assembly between the annular projections of the respective axial member components. Additional medical devices can be mounted by coupling additional axial components.

In a fourth embodiment, methods of coating a medical device include the step of applying a coating solution containing a therapeutic agent to the abluminal surface of the medical device mounted on the mandrel coating assembly. During a spray coating process, a spray of the coating solution may pass through openings in the medical device and contact the axial member of the mandrel coating assembly. Preferably, the axial member and the spray are dimensioned such that the spray does not extend past the axial member. For example, a spray having a substantially circular transverse cross-sectional area impinging the axial member may be centered on the axial member with a diameter that is less than the diameter of the axial member.

DETAILED DESCRIPTION

Figure 1:
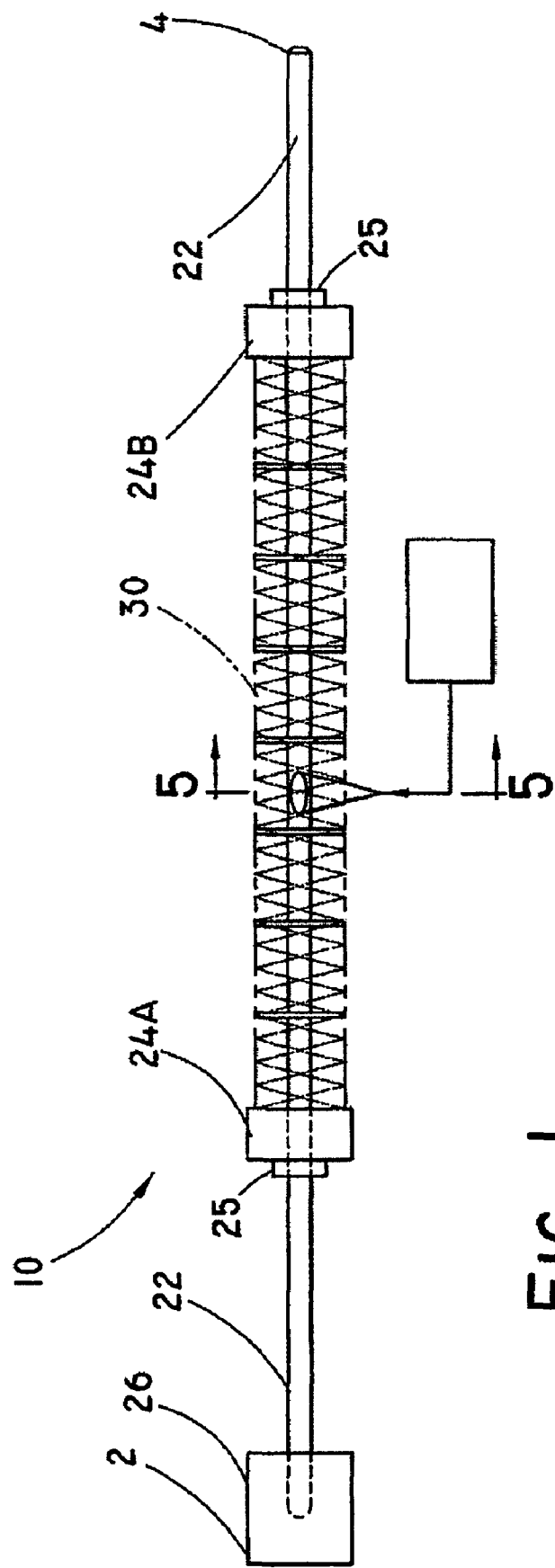
FIG. 1 is a side view of a first mounted endoluminal medical device coating assembly.

The present disclosure relates to methods of coating an endoluminal medical device, and mandrels configured to coat an endoluminal medical device. For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The term "coating," as used herein and unless otherwise indicated, refers generally to material attached to an implantable medical device. A coating can include material covering any portion of a medical device, and can be configured with one or more coating layers. A coating can have a substantially constant or a varied thickness and composition. Coatings can be adhered to any portion of a medical device surface, including the luminal surface, the abluminal surface, or any portions or combinations thereof.

As used herein, the terms "proximal" and "distal" describe longitudinal directions in opposing axial ends of a mounted endoluminal medical device coating assembly, and components thereof.

As used herein, "securing contact" between an annular projection and a medical device refers to physical contact between a surface of the annular projection and a surface of the medical device that is effective to maintain the medical device in a fixed orientation with respect to the axial member during translational or rotational movement of the axial member.

As used herein, the phrase "therapeutic agent" refers to any pharmaceutically active agent that results in an intended therapeutic effect on the body to treat or prevent conditions or diseases. Preferably, the therapeutic agent is an agent effective to treat or prevent restenosis, such as an antisense agent, a microtubule stabilizing agent or an inhibitor of the mammalian target of rapamycin (mTOR). Preferred therapeutic agents include the paclitaxel [β-(benzoylamino)-α-hydroxy-, 6,12b-bis-(acetyloxy)-12-(benzoyloxy)-2a,3,4,4a,5,6,9,10, 11,12,12a,12b-dodecahydro-4,11-dihydroxy-4a,8,13,13-tetramethyl-5-oxo-7,11-methano-1H-cyclodeca(3,4)benz(1,2-b)-oxet-9-ylester,(2aR-(2a-α,4-β,4a-β,6-β,9-α-(α-R*,β-S*), 11-α, 12-α, 12a-α,2b-α))-benzenepropanoic acid] and bupivacaine [1-butyl-N-(2,6-zimethylphenyl)piperidine-2-carboxamide].

In a first embodiment shown in FIG. 1, a mandrel coating assembly 10 extends from a proximal end 2 to a distal end 4 and includes an axial member 22 and one or more annular projections, such as the pair of spacing rings 24a, 24b extending radially from the axial member 22. The annular projections may have a diameter that is greater than the diameter of the axial member 22 and are securely attached to the axial member 22 such that translational and rotational motion of the axial member 22 is uniformly and efficiently imparted to the annular projections. Preferably, the annular projections have substantially similar ring shapes and have at least one surface configured to securely contact a medical device 30 mounted on the coating assembly 10. Annular projections may be configured to fit within the lumen of a mounted medical device, and/or between axially stacked, longitudinally adjacent mounted medical devices.

The pair of spacing rings 24a, 24b may be attached to the axial member 22 by welding or soldering each spacing ring 24a, 24b at a fixed longitudinal distance from each other. Optionally, a first spacing ring 24a may be affixed to the axial member 22, while a second spacing ring 24b may be translated along the axial member 22 and locked into place at a desired position. In another example, both the first spacing ring 24a and second spacing ring 24b can be translated along the axial member 22 into place at a desired position, usually to optimize the spray pattern. For instance, the axial member 22 and the second spacing ring 24b may include a means 25 for securing the first spacing ring 24a, the second spacing ring 24b, or both, at one or more positions along the axial member 22, such as an interlocking set of complementary projections and apertures on the spacing rings 24a, 24b and the axial member 22. Other examples of the means 25 of securing can include other mechanical means, including adhesives, soldering, a collet, a flexible member with a high coefficient of friction, such as a silicone tubular member with a slit, which can allow the flexible member to be easily removed and reapplied at the desired location. The annular projections are preferably formed from the same material as the axial member 22, although they may be formed from any material that may be fixedly attached to the axial member 22 and have sufficient rigidity to translate physical motion of the axial member 22 to a medical device in securing contact with the annular projection.

Figure 2A:
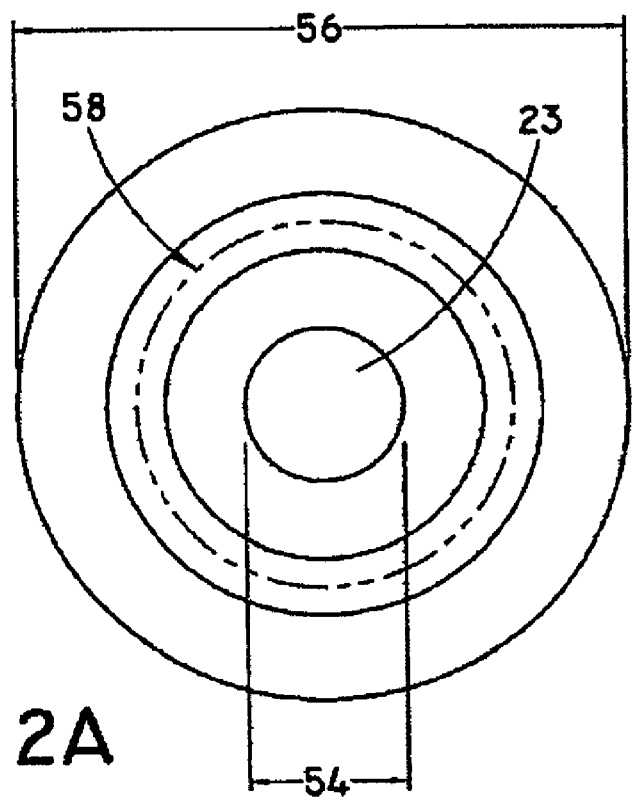
FIG. 2A is a detailed end view of an annular support ring.

FIG. 2A is a detailed side view of the spacing ring 24b, an annular ring having an outer diameter 56 and an inner diameter 54 enclosing a hole 23. The inner diameter 54 may be substantially equal to the outer diameter of the axial member 22 and hole 23 is configured to receive the axial member 22. The spacing ring 24b may be adapted to slide along the axial member 22 from the distal end 4 in the proximal direction to a desired position, where the spacing ring 24b may be secured to the axial member by the means for securing 25. The outer diameter 56 is typically greater than the outer diameter of the vascular stent 30. Accordingly, the spacing ring 24b may include a groove 58 having a diameter substantially equal to the diameter of the vascular stent 30 in the expanded configuration and having a thickness approximately equal to or greater than the thickness of the vascular stent 30.

Figure 2B:
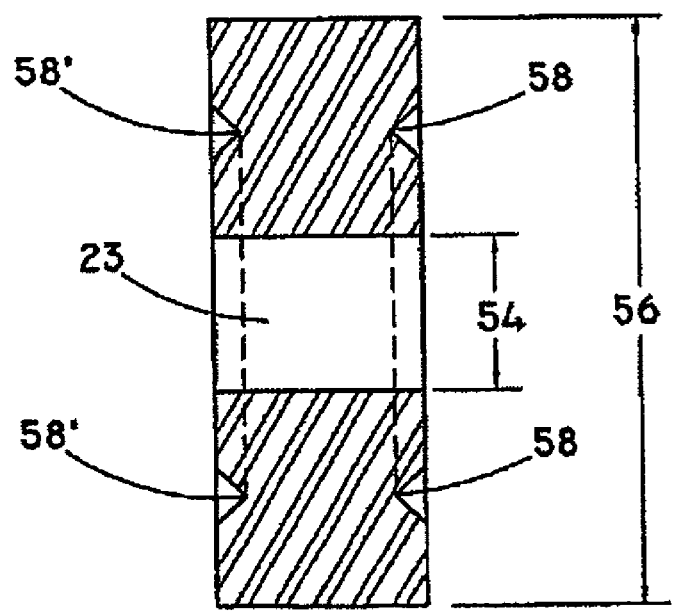
FIG. 2B is a transverse cross sectional view of the annular support ring shown in FIG. 2A.

FIG. 2B shows a transverse cross sectional view of the spacing ring 24b shown in FIG. 2A, including the hole 23, inner diameter 54, outer diameter 56 and groove 58. In addition, the spacing ring 24b may also have a second groove 58' on the side opposite the first groove 58. The second groove 58' may be otherwise identical to the first groove 58 or optionally may have a different diameter. The grooves 58, 58' are preferably a V-shaped groove having 60° sides, but can be any angle suitable to support a tubular medical device and/or to minimize the covering of the edge. Optionally, the grooves can be rectangular or even U-shaped suitable for the same purpose. Examples of preferred ratios between the radius of the groove 58 may be about 60-75% of the outer diameter 56, including groove 58 radii that are 62%, 69% and 74% of the outer diameter 56. The spacing ring 24b may be made from any suitable material, such as 302 stainless steel.

A tubular medical device, such as a vascular stent 30, may be positioned around the mandrel coating assembly 10. The tubular medical device preferably includes a plurality of holes between the abluminal surface and the luminal surface defining a cylindrical lumen extending longitudinally through the tubular medical device. In general, the tubular medical device may comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of intraluminal stents include endovascular, biliary, tracheal, gastrointestinal, urethral, ureteral, esophageal and coronary vascular stents. The intraluminal stents of the present invention may be, for example, balloon-expandable or self-expandable. A vascular stent 30 may include a plurality of interconnected struts and bends in a plurality of longitudinally connected sinusoidal hoop members. The tubular medical device may be radially expandable from a compressed configuration to a radially expanded configuration. The vascular stent 30 is shown in an expanded configuration including a lumen with a first diameter. The inner diameter of the lumen is preferably greater than the diameter of the axial member 22. More specifically, the vascular stent 30 may be, for example, a Wallstent, Palmaz-Shatz, Wiktor, Strecker, Cordis, AVE Micro Stent, Igaki-Tamai, Millenium Stent (Sahajanand Medical Technologies), Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Tecnic stent (Sorin Biomedica), BiodivYsio (Abbott), Trimaxx (Abbott), DuraFlex (Avantec Vascular), NIR stent (Boston Scientific), Express 2 stent (Boston Scientific), Liberte stent (Boston Scientific), Achieve (Cook/Guidant), S-Stent (Guidant), Vision (Guidant), Multi-Link Tetra (Guidant), Multi-Link Penta (Guidant), or Multi-Link Vision (Guidant). Some exemplary stents are also disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau. Desirably, the stent is a vascular stent such as the commercially available Gianturco-Roubin FLEX-STENT®, GRII™, SUPRA-G, ZILVER or V FLEX devices from Cook Incorporated (Bloomington, Ind.).

The vascular stent 30 may be mounted on the mandrel coating assembly 10 between the first spacing ring 24a and the second spacing ring 24b. Each spacing ring 24a, 24b may have a diameter that is greater than both the axial member 22 and the diameter of the lumen of the vascular stent 30 in the expanded configuration. Preferably, no portion of the spacing rings 24a, 24b extends through openings in the mounted vascular stent 30. The proximal and distal ends of the vascular stent 30 may be in securing contact with the first spacing ring 24a and the second spacing ring 24b, respectively, to maintain the vascular stent 30 in a floating position. In other words, the luminal surface of the vascular stent 30 can be spaced apart from and substantially parallel to the axial member 22. The luminal surface of the vascular stent 30 preferably does not contact the axial member 22 in order to reduce the potential of coating irregularities such as "webbing."

The vascular stent 30 may be positioned and mounted on the mandrel coating assembly 10 by: (1) removing the second spacing ring 24b from the mandrel coating assembly 10, (3) positioning the vascular stent 30 around the distal end of the axial member 22, (4) longitudinally translating the vascular stent 30 toward the proximal end of the mandrel coating assembly 10 until the proximal end of the vascular stent 30 contacts the first spacing ring 24a, (5) positioning the second spacing ring 24b around the distal end of the axial member 22 and sliding the second spacing ring 24b toward the proximal end 2 of the mandrel coating assembly 10 to bring the second spacing ring 24b into securing contact with the distal end of the vascular stent 30 and (6) securing the second spacing ring 24b to the axial member 22 to secure the vascular stent 30 to the mandrel coating assembly 10. Alternatively, one or more spacing rings 24a, 24b having a diameter greater than that of the vascular stent 30 may be positioned at both ends of the vascular stent 30, with each spacing ring adapted to retain the vascular stent 30 substantially parallel to, and spaced apart from, the axial member 22. Preferably, the vascular stent 30 does not contact the axial member 22.

The axial member 22 may be a solid cylindrical member oriented along a longitudinal axis of the coating assembly 10, and may be formed from a rigid material adapted to translate rotational force from the proximal shaft mount 26 throughout the length of the axial member 22. For example, the axial member 22 may be a stainless steel mandrel having a substantially uniform circular transverse cross-section with a substantially uniform diameter along the length of the mandrel. The proximal shaft mount 26 may have a circular transverse cross-section with a diameter that is greater than the diameter of the medical device positioned around the axial member 22 when mounted to the mandrel coating assembly 10.

Preferably, the mandrel coating assembly is rotated while coating a medical device mounted thereto. The axial member 22 may be attached to a means for imparting rotational motion to the axial member 22. In FIG. 1, the distal end of a proximal shaft mount 26 is adapted to securely receive the proximal end of the axial member 22 and impart rotational motion thereto. The axial member 22 may be secured to the proximal shaft mount 26 by any conventional means, including a screw, bolt, adhesive, weld or other retaining means.

Figure 3A:
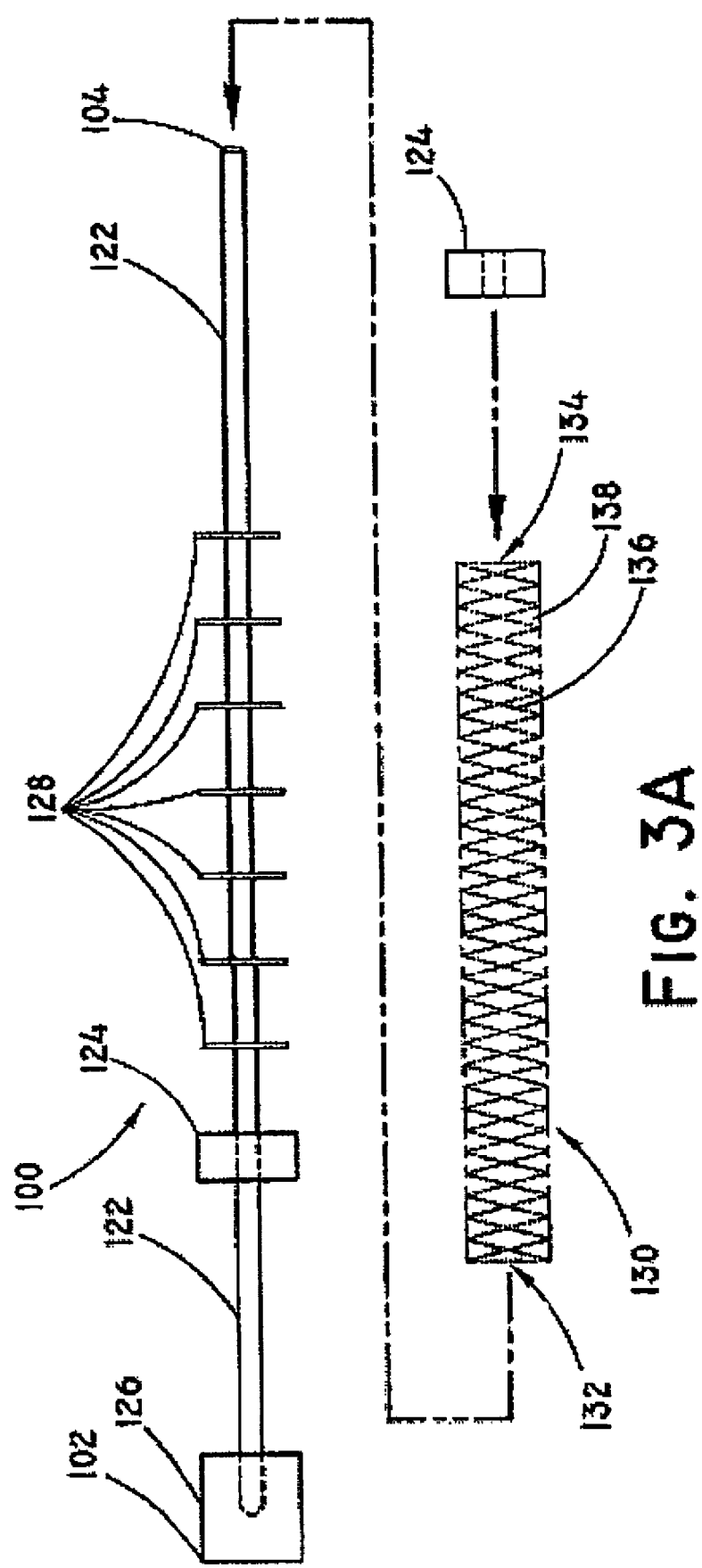
FIG. 3A is a side view of a second coating assembly.

FIG. 3A shows a second exemplary mandrel coating assembly 100 extending from a proximal end 102 to a distal end 104 and including an axial member 122 of a first diameter and a proximal end secured to a rotating proximal shaft mount 126. A plurality longitudinally spaced annular support rings 128 positioned between a pair of spacing rings 124 are together disposed along the length of the axial member 122. The annular support rings 128 may have a second diameter that is greater than the first diameter of the axial member 122; the spacing rings 124 may have a third diameter that is greater than the second diameter. Preferably, the annular support rings 128 have a second diameter that is substantially similar to the diameter of the luminal surface of a vascular stent.

The vascular stent 130 may be positioned around and mounted to the mandrel coating assembly 100. The vascular stent 130 may include a plurality of interconnected struts 136 defining a plurality of openings 138 radially extending between an abluminal (outer) surface and a luminal (inner) surface defining a cylindrical lumen with a fourth diameter extending from a proximal end 132 to a distal end 134. The fourth diameter is preferably substantially equal to the second diameter of the annular support rings 128. The distal spacing ring 124 may be removed from the axial member 122 prior to positioning and mounting the vascular stent 130. The vascular stent 130 is positioned around the distal end of the axial member 122 and translated toward the proximal end 102 of the mandrel coating assembly 100 until the proximal end 132 of the vascular stent 130 contacts a spacing ring 124. The luminal surface of the vascular stent 130 may be mounted by placing the luminal surface of the vascular stent 130 in securing contact with the plurality of annular support rings 128 positioned within the lumen. The luminal surface of the mounted vascular stent 130 may be oriented substantially parallel to and spaced apart from the axial member 122. A spacing ring 124 may be subsequently positioned around the axial member 122 and longitudinally translated into contact with the distal end 134 of the mounted vascular stent 130. The spacing ring 124 can be affixed to the axial member 122 by the means 125 for securing.

Figure 3B:
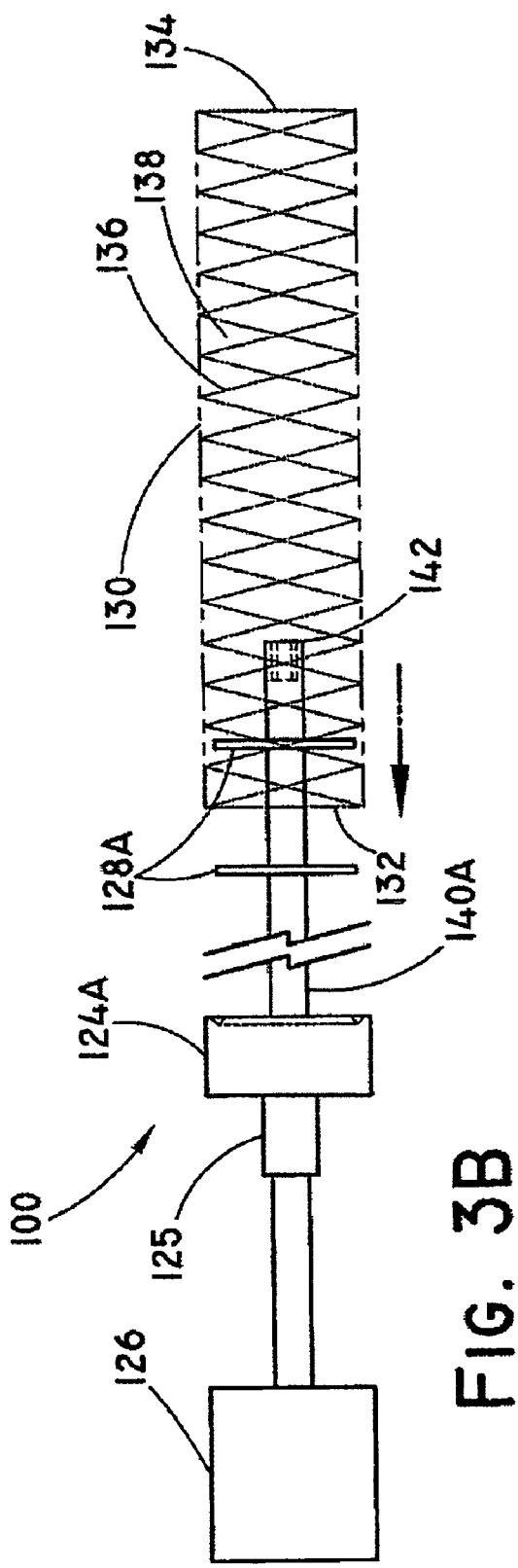
FIG. 3B is a side view of third coating assembly with a first axial member component.

FIG. 3B illustrates the mandrel coating assembly that can be broken into components that can assist in the positioning and mounting of the vascular stent 130 around the mandrel coating assembly 100. A first axial member component 140a can have a proximal end that is secured to a rotating proximal shaft mount 126. The first axial member 140a can include a spacing ring 124a that can be translated along the first axial member component 140a and affixed to the first axial member component 140a at a desired location by the means 125 for securing. The first axial member component 140a can also include a plurality of annular support rings 128a. At the distal end of the first axial member component 140a is a coupling means 142. The coupling means 142 can be quickly engaged and disengaged with another axial member component. In FIG. 3B the coupling means 142 at the distal end of the first axial member component 140a is a tapped hole (female) to be threadably engaged with threaded shaft (male) of another axial member component. Other examples of the coupling means 142 can include pin, friction fitting, compression fitting, or any other suitable coupling means.

The vascular stent 130 is positioned around the distal end of the first axial member component 140a and translated toward the proximal end of the mandrel coating assembly 100 until the proximal end 132 of the vascular stent 130 contacts the spacing ring 124a. The luminal surface of the vascular stent 130 may be mounted by placing the luminal surface of the vascular stent 130 in securing contact with the plurality of annular support rings 128a positioned within the lumen. The luminal surface of the mounted vascular stent 130 may be oriented substantially parallel to and spaced apart from the axial member 122.

Figure 3C:
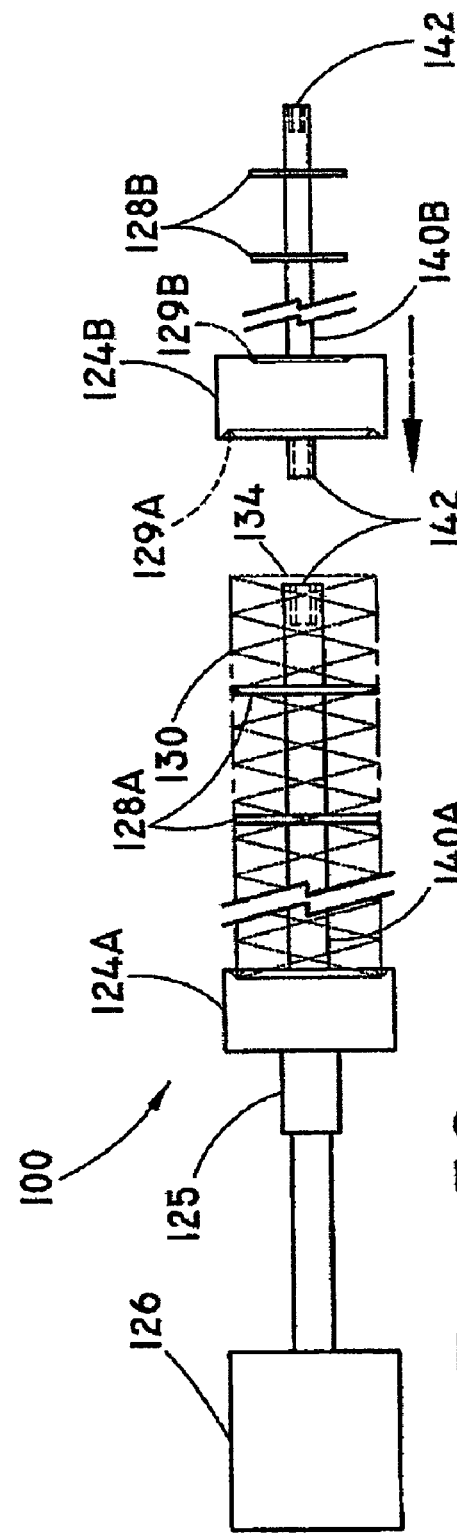
FIG. 3C is a side view of the third coating assembly shown in FIG. 3B with a first axial member component and a second axial member component.

A second axial component 140b can include a spacing ring 124b that can be affixed to the second axial member component 140b. The second axial member component 140b can also include the plurality of annular support rings 128b. At the distal end, the proximal end, or both, of the second axial member component 140b are the coupling means 142. In FIG. 3C the coupling means 142 at the proximal end of the second axial member component 140b is a threaded shaft (male) and at the distal end of the second axial member component 140b is a tapped hole (female). The proximal end of the second axial member component 140b is coupled to the distal end of the first axial member component 140a, causing the spacing ring 124b of the second axial member component 140b to be longitudinally translated into contact with the distal end 134 of the mounted vascular stent 130. Additional axial member components can be coupled to the mandrel coating assembly 100 depending on the number of vascular stents to be coated. Each axial member component can have a uniform diameter that is less than the diameter of the lumen of the vascular stent 130.

To accommodate simultaneously coating vascular stents having different diameters, the diameters of the axial member components 140a, 140b, the annular spacing rings 124a, 124b, the annular grooves 58, 58' and the annular support rings 128a, 128b can vary proportionally to the diameter of the respective vascular stent. For example, the second axial member component 140b in FIG. 3C is sized for a smaller vascular stent. The diameter of the second axial member component 140b is less than the diameter of the first axial member component 140a. The diameter of the annular support rings 128b of the second axial member component 140b is less than the diameter of the annular support rings 128a of the firs axial member component 140a. Likewise, the diameter of the spacing ring 124b of the second axial member component 140b is less than the diameter of the spacing rings 124a of the first axial member component 140a. The spacing ring 124b of the second axial member component 140b also includes grooves 129a, 129b having different diameters corresponding to the vascular stents on the proximal side and the distal side of the spacing ring 124b.

For better support during the process, especially for longer stents (greater than about 30-40 mm), the annular support rings 128 can be included on the axial member 122. The annular support rings 128 can be machined with the axial member 122 as a single piece or can be machined separately and attached by mechanical means, such as adhesives, soldering, or the like. Preferably, the edge of the annular support rings 128 is shaped to a point or tip to minimize contact with the substantially all of the luminal surface of the vascular stent 130 where the edge contacts. The annular support rings 128 can be spaced by any suitable dimension (generally up to 30 mm) to prevent the vascular stent 130 from sagging and/or to keep the abluminal surface of the vascular stent a uniform distance from the coating nozzle. For example, for a 60 mm vascular stent, one support ring can be provided at about 30 mm from the spacing rings. Alternatively, two support rings can be provided at about 20 mm from the spacing rings and each other.

Figure 4:
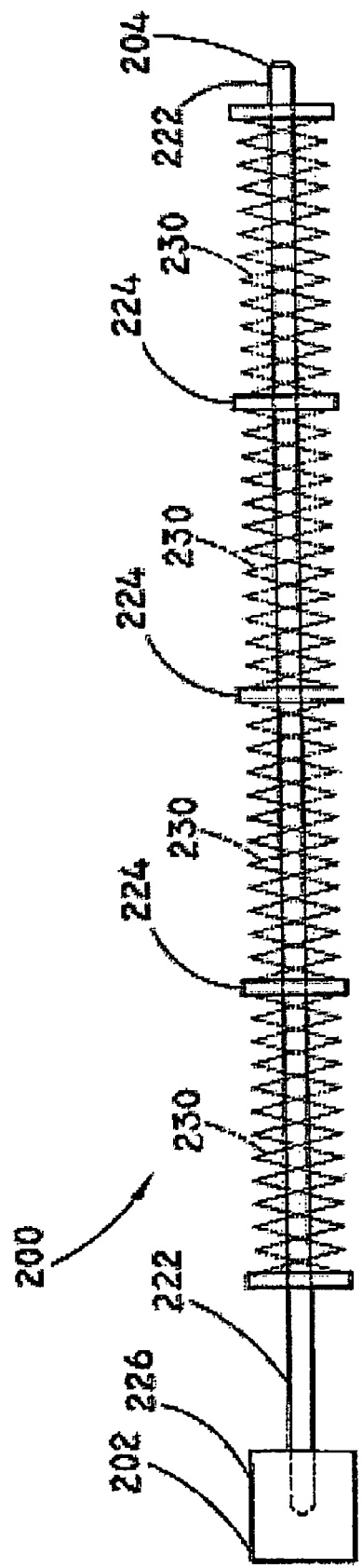
FIG. 4 is a side view of a third mounted endoluminal medical device coating assembly.

A plurality of tubular medical devices may be mounted on a mandrel coating assembly. FIG. 4 shows a third mandrel coating assembly 200 extending from a proximal end 202 to a distal end 204, and including an axial member 222 attached to a proximal shaft mount 226 adapted to rotate the axial member 222 around the longitudinal axis of the mandrel coating assembly 200. The mandrel coating assembly 200 may include a plurality of spacing rings 224 having an inner diameter that is substantially equal to the outer diameter of the axial member 222. Each spacing ring 224 is attached to the axial member 222 by the means for securing 125. A series of tubular medical devices 230 can be mounted with the luminal surface of each medical device 230 in securing contact with spacing rings 224. The inner diameter of the medical devices 230 can be substantially equal to the outer diameter of the spacing rings 224. Alternatively, the series of tubular medical devices 230 can be mounted with the proximal and distal ends of each medical device 230 in securing contact with an annular groove 58, 58' in the spacing rings 224. The inner diameter of the medical device 230 can be less than the outer diameter of the spacing rings 224. The luminal surfaces of the mounted medical devices 230 are maintained substantially parallel to and spaced apart from the outer surface of the axial member 222. Rotation and translation of the axial member 222 is imparted to the mounted medical devices 230.

Figure 5:
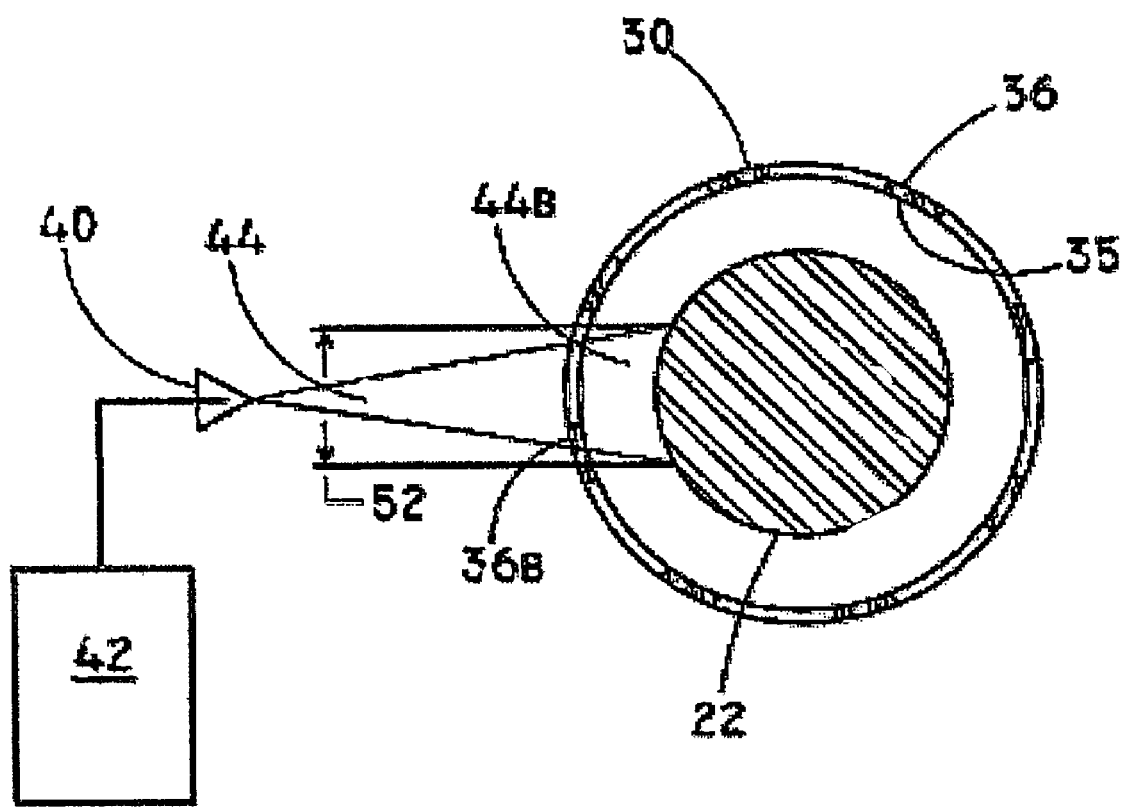
FIG. 5 is a transverse cross-sectional view of a portion of the first coating assembly in FIG. 1 during spray coating of the mounted endoluminal medical device.

A medical device mounted on a mandrel coating assembly (e.g., as shown in FIGS. 1-3) may be coated with a therapeutic agent. The mandrel coating assembly may be configured to localize coating of the therapeutic agent to the abluminal surface of the medical device, prevent or reduce coating irregularities such as "webbing," and improve coating uniformity. A therapeutic agent may be applied by spraying a coating solution including the therapeutic agent and a solvent onto the abluminal surface of the tubular medical device mounted on the mandrel coating assembly. FIG. 5 is a cross sectional view along line 5-5 in FIG. 1, showing a coating solution spray 44 exiting a nozzle 40 and contacting the abluminal surface of the vascular stent 30. The coating solution 42 containing a therapeutic agent is passed through the nozzle 40 in a manner effective to atomize the coating solution 42 to form the spray 44. A portion 44b of the spray 44 passes through the holes through a portion 36b of the abluminal surface 36 of the vascular stent 30 and contacts the axial member 22. Preferably, the shape of the spray 44 may be a conical plume controlled such that the maximum distance 52 across the spray 44 is less than the diameter of the axial member 22. The shape of the spray 44 may be controlled by the size and shape of the nozzle 40 and the pressure applied to the coating solution 42. The spray 44 preferably terminates at the axial member 22. That is, the axial member 22 may have an outer diameter large enough to occlude the spray 44 from directly contacting the luminal surface 35 of the vascular stent 30 opposite the position of the nozzle 40. However, a portion of the spray 44 may indirectly contact the luminal surface of the vascular stent 30 by deflection of the spray 44 from the abluminal surface or edges of the vascular stent 30 during spray coating. The mounted vascular stent 30 is maintained substantially parallel to and spaced apart from the axial member 22, and is preferably rotated during the spray coating process. The nozzle 40 may be rastered longitudinally along the length of the axial member 22 to apply a coating along the length of the vascular stent 30.

Preferably, the therapeutic agent is coated onto an implantable medical device by an ultrasonic spray deposition (USD) process. The medical device may be coated using an ultrasonic spray nozzle 40, such as those available from Sono-Tek Corp., Milton, N.Y. Ultrasonic nozzles employ high frequency sound waves generated by piezoelectric transducers which convert electrical energy into mechanical energy. The transducers receive a high frequency electrical input and convert this into vibratory motion at the same frequency. This motion is amplified to increase the vibration amplitude at an atomizing surface. The ultrasonic nozzle may be configured such that excitation of the piezoelectric crystals creates a longitudinal standing wave along the length of the nozzle. The ultrasonic energy originating from the transducers undergoes a step transition and amplification as the standing wave traverses the length of the nozzle. The nozzle is designed such that a nodal plane is located between the transducers. For ultrasonic energy to be effective for atomization, the nozzle tip is preferably located at an anti-node, where the vibration amplitude is greatest. To accomplish this, the nozzle's length is preferably a multiple of a half-wavelength. In general, high frequency nozzles are smaller, create smaller drops, and consequently have smaller maximum flow capacity than nozzles that operate at lower frequencies.

A spray solution 42 introduced onto the atomizing surface absorbs some of the vibrational energy, setting up wave motion in the liquid on the surface. For the liquid to atomize, the vibrational amplitude of the atomizing surface should be carefully controlled. Below a certain critical amplitude, the energy is insufficient to produce atomized drops. If the amplitude is excessively high, cavitation occurs. Only within a narrow band of input power is the amplitude ideal for producing the nozzle's characteristic fine, low velocity mist. Since the atomization mechanism relies only on liquid being introduced onto the atomizing surface, the rate at which liquid is atomized depends solely on the rate at which it is delivered to the surface. The spray solution 42 may be loaded into a syringe, which is mounted onto a syringe pump and connected to a tube that carries the solution to the ultrasonic nozzle. The syringe pump is then used to purge the air from the solution line and prime the line and spray nozzle with the solution.

The stent is loaded onto a mandrel in the ultrasonic coating chamber. The stent is held on a mandrel by the annular projections. The stent is floating, i.e., does not touch any part of the mandrel, preventing a webbed coating between struts, and the luminal surface is not coated. The medical device may be a stent 6-8 mm in diameter that is mounted on a mandrel coating assembly. Other sized stents and mandrels may also be used in the present invention. The mandrel is fastened onto a motor, positioned below the ultrasonic nozzle. The motor rotates the mandrel at a pre-set speed and translationally moves it so that all parts of the stent pass underneath the ultrasonic spray. In one embodiment, the rotational speed is set to 10 rpm and the translational speed is set to 0.01 mm per second. In another embodiment, the rotational speed is set to 60 rpm and the translational speed is set to 0.05 mm per second. In yet another embodiment, the rotational speed is set to 30-150, preferably about 110 rpm, and the translational speed is set to 0.19 mm per second. Other speeds and combinations may also be used in the present invention. Preferred coating parameters for USD using a Sono-tek Model 8700-60 ultrasonic nozzle are provided in Table 1 below.

TABLE 1

| Ultrasonic Spray Deposition Parameters for Sono-tek Model 8700-60 | | | | | |
|---|---|---|---|---|---|
| Flow rate (mL/min) | Coating velocity (in/sec) | Rotation Speed (rpm) | Nozzle Power (watts) | Process Gas (psi) | Distance (mm) |
| 0.01-2 | 0.01-0.5 | 30-150 | 0.9-1.2 | 0.1-2.5 | 1-25 |

The coating is preferably applied within an enclosed chamber purged with nitrogen to displace oxygen in the system. During the process, the stent is kept at ambient temperature and in a closed chamber.

The coating solution 42 preferably includes a therapeutic agent and a solvent. The solvent may be selected to dissolve the therapeutic agent and readily evaporate within the spray 44 or on the abluminal surface of the vascular stent 30. A coating comprising a therapeutic agent can be formed on the abluminal surface of the medical device by applying the coating solution 42 consisting essentially of the therapeutic agent and an evaporative solvent. In one aspect, the coating solution 42 does not contain a bioabsorbable elastomer. For example, the therapeutic agent may be paclitaxel and the solvent may be ethanol or methanol. A coating solution 42 of about 0.5-5.0 mM paclitaxel in ethanol may be used, and preferably, coating solution 42 includes 0.7 mM or 1.2 mM paclitaxel in ethanol. Other therapeutic agents and solvents may also be used in solutions at concentrations permitting desirable deposition rates forming coatings with desired durability.

Optionally, a biodegradable material, such as a bioabsorbable elastomer (such as PLA) may also be sprayed onto the medical device, and is preferably dissolved in a solvent mixture comprising a mixture of dichloromethane:methanol in a 1:2 (+/−10%) ratio by volume. For example, the solvent mixture can comprise about 50-80% methanol and about 20-50% dichloromethane (by volume). More desirably, the mixture is about 65-75% methanol and about 25-40% dichloromethane (by volume). Even more desirably, the mixture is about 70% methanol and about 30% dichloromethane (by volume). It is believed that the addition of methanol to dichloromethane can increase the polarity of the solvent solution, thereby providing a fine spray that is ideal when using an electrostatic coating process. This solvent combination may provide a smooth, uniform bioabsorbable elastomer coating when applied by spraying.

The bioabsorbable elastomer may be a polyhydroxyalkanoate compound, a hydrogel, poly(glycerol-sebacate) or an elastin-like peptide. Desirably, the bioabsorbable elastomer includes a polyhydroxyalkanoate bioabsorbable polymer such as polylactic acid (poly lactide), polyglycolic acid (poly glycolide), polylactic glycolic acid (poly lactide-co-glycolide), poly-4-hydroxybutyrate, or a combination of any of these. Desirably, the bioabsorbable elastomer comprises a poly-α-hydroxy acid, such as polylactic acid (PLA). PLA can be a mixture of enantiomers typically referred to as poly-D, L-lactic acid. Alternatively, the bioabsorbable elastomer is poly-L(+)-lactic acid (PLLA) or pol-D(−)-lactic acid (PDLA), which differ from each other in their rate of biodegradation.

Optionally, the coating method may be repeated after the application of the therapeutic agent coating to the abluminal surface of the medical device. A second layer comprising a bioabsorbable elastomer material can be dissolved in a solvent to form a second coating solution 42 that may be subsequently sprayed onto a layer of therapeutic agent that was previously deposited on the medical device. Desirably, the polymer is PLA and the solvent is dichloromethane. More desirably, about 0.1-7.0 g/L of PLA in dichloromethane is used. Even more desirably, about 2.5-6.5 g/L and most desirably, 5.0 g/L of PLA in dichloromethane is used. A second coating solution of about 2-4 g/L of a bioabsorbable elastomer such as PLA in a suitable solvent such as dichloromethane can be applied using an ultrasonic nozzle.

Multiple coating layers may be separately applied sequentially using an ultrasonic nozzle spray coating technique employing ultrasound to atomize the spray solution to provide a smooth and uniform polymer coating. Preferably, the polymer coating is applied from an ultrasonic nozzle.

EXAMPLES

Example 1

Ultrasonic Spray Coating of Stents with Paclitaxel

Stents with coatings consisting of paclitaxel may be prepared by spray coating a solution comprising paclitaxel, methanol and water. A 1.74 mM paclitaxel solution may be prepared in 68% methanol by dissolving 7.43 mg of paclitaxel in 5 mL of previously made solution of 68% methanol 32% water. The solution may be sprayed from an ultrasonic spray gun (Sono-tek Model 06-04372) in a glove box. Before spraying, the glove box may be purged with nitrogen at 20 psi for 15 minutes. The atmosphere in the glove box may be adjusted until the oxygen meter reads a constant 200 ppm within the glove box. The heat in the glovebox may be set to 31° C. (88° F.), the air shroud to 2.0 psi and the ultrasonic power to 1.0 W. The paclitaxel solution may be loaded into a syringe and placed on the syringe pump in the ultrasonic coating apparatus and a bare metal stent (for example, 6×20 ZILVER, Cook Inc., Bloomington, Ind.) may be mounted on a mandrel aligned with the spray nozzle. The solution may be sprayed onto a stent using a 60 kHz nozzle at a flow rate of 0.03 mL/min, a coating velocity of 0.025 in/sec, a nozzle power of 1.0 W, a process gas pressure of 2.0 psi, and a distance from the nozzle to the stent of about 12 mm, while rotating the stent with an axial rotation rate of 60 rpm. A mandrel coating assembly described above is used, with the diameter of the axial member being larger than the maximum width of the spray contacting the axial member. Only the abluminal surface of the stent is coated.

Example 2

Single Layer of PLA Over Single Layer of Paclitaxel on a Stent Using Ultrasonic Deposition Method Paclitaxel may be applied to a Zilver® stent by dissolving Paclitaxel in ethanol at a concentration of about 2.4 mM as described in Example 1.

Optionally, once the stents are coated with the paclitaxel, a biodegradable PLA polymer is applied by dissolving 2 to 4 g/L in dichloromethane (a second coating solution). The second coating solution may be applied by using the ultrasonic nozzle. The second coating solution is loaded into a 10.0 mL syringe, which is mounted onto a syringe pump and connected to a tube that carries the solution to a spray head. The syringe pump is then used to purge the air from the solution line and prime the line and spray nozzle with the solution. The ultrasonic nozzle is arranged such that excitation of the piezoelectric crystals generates a transverse standing wave along the length of the nozzle. The solution introduced onto the atomizing surface may absorb some of the vibrational energy, creating a wave motion in the liquid. For the liquid to atomize, the vibrational amplitude of the atomizing surface may be carefully controlled. The coating chamber is purged with nitrogen to displace any oxygen in the system One end of the stent is slipped onto a mandrel and half of the stent is coated. The nozzle is manually aligned to the tip of the stent and the middle of the stent. These position numbers are used for the coating program when the syringe pump is actually activated. Next, the stent orientation is reversed and the other half is coated. During the process, the stent is kept at ambient temperature and in a closed chamber.

TABLE 2

Process Parameters for Ultrasonic Coating

| Flow rate (mL/min) | Coating velocity (in/sec) | Rotation Speed (rpm) | Nozzle Power (watts) | Process Gas (psi) | Distance (mm) |
|---|---|---|---|---|---|
| 0.01-2 | 0.005-0.5 | 30-150 | 0.9-1.2 | 0.1-2.5 | 1-25 |

Alternatively, the coating solution 42, and the various solutions described herein, may be applied using an electrostatic spray deposition (ESD) process by an electrostatic spraying apparatus (Teronics Development Corp.). The ESD process may especially be desirable when the therapeutic agent is hydrophilic. The solution that is to be deposited on the target is typically charged to several thousand volts (typically negative) and held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the electrons are further attracted towards the metal portions of the target, rather than towards the non conductive base the target is mounted on, leaving the coating mainly on the target only. Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

Alternatively, the coating solution 42, and the various solutions described herein, may be applied using a pressure spray gun. One example is the pressure spray gun manufactured (notorious for cloud of spray) by Badger (Model No. 200), in a fume hood, with a fluid dispensing system connected to a pressure source (nitrogen) until the target dose of drug is reached. Adjustments on the system may be made to control the spray pattern and the amount of fluid dispensed. The spray gun may be aligned with the stents by setting a laser beam even with the nozzle of the spray gun and positioning the stents so that the laser beam is located at approximately ¼ the distance from the top of the stents. The spray gun, which may be positioned parallel to the hood floor and at a horizontal distance of approximately 5-7 inches from the stents, may then be passed over the surface of the stents until a predetermined volume of spray is dispensed. The stents may then be rotated approximately 90° and the spraying procedure may be repeated until the entire circumference of each stent is coated. The movement of the gun may be slow enough to allow the solvent to evaporate before the next pass of the gun. Each spray application may cover approximately 90° of the circumference of the stents. The stents may be kept at ambient temperature and humidity during the spraying process. After substantially all of the solvent has evaporated, a coating of paclitaxel is left on the abluminal surface of the stent.

Example 3

Stents Coated with Single Layer of Therapeutic Agent

Paclitaxel may be applied to Zilver® stents (nitinol stents manufactured by Cook Inc., Bloomington, Ind.) ranging in size from about 6×20 mm to about 14×80 mm, or any size, as follows. First, paclitaxel can be dissolved in ethanol to form a 2.4 mM solution. The paclitaxel may be substantially dissolved within about 30 minutes, using sonication. This solution may be used to set the flow rate of the spray gun to the target flow rate of approximately 5.7 ml/min. The stent is held on a mandrel by the annular projections. The stent is floating, i.e., does not touch any part of the mandrel, preventing a webbed coating between struts, and the luminal surface is not coated. Approximately 25 ml of the paclitaxel solution may be added to the spray gun reservoir of the pressure spray gun. The coating solution 42 may be applied using a pressure spray gun, in a fume hood, with a fluid dispensing system connected to a pressure source (nitrogen) until the target dose of paclitaxel is reached.

Example 4

Single Layer of PLA Over Single Layer of Paclitaxel on a Stent Using Pressure Gun Spray Coating Method Paclitaxel may first be applied to Zilver® stents (nitinol stents manufactured by Cook Inc., Bloomington, Ind.) ranging in size from about 6×20 mm to about 14×80 mm (or any size), as described in Example 3.

After the paclitaxel layer has air dried, a layer of PLA may be spray deposited over the paclitaxel coating using the same type of pressure spray coating apparatus as Example 3. A second coating solution of approximately 2-4 g/L of PLA in dichloromethane may be prepared without paclitaxel, filtered over a 0.2 micron nylon filter, and collected in a flask. The second coating solution may then be sprayed over the coating of paclitaxel on the abluminal surface of the stent using a procedure similar to the one described above with respect to Example 3. For PLA, however, the spraying may be performed at two different heights. First, the stents may be positioned with the spray gun nozzle positioned between the midpoint and the proximal end, sprayed, and rotated until the circumference of the top portion of the stents are coated. Next, the stents may be positioned with the spray gun nozzle positioned between the midpoint and the distal end, sprayed, and rotated until the circumference of the bottom portion of the stents are coated.

Example 5

Single Layer of PLA Over Single Layer of Paclitaxel on a Stent Using Electrostatic Spray Deposition Method Approximately 1-25 micrograms of paclitaxel may be applied to a Zilver® stent by dissolving paclitaxel in ethanol (using sonication) at a concentration of about 2.4 mM and applying the solution to a stent with the electrostatic spraying apparatus. Specifically, the solution may be loaded into a 20 mL syringe, which is then mounted onto a syringe pump and connected to a tube that carries the solution to a spray head. The syringe pump may be used to purge the air from the solution line and prime the line and spray nozzle with solution. An electrical connection to the nozzle may supply the required voltage. The stent may be slipped over a mandrel (Teronics Development Corp., 6 mm×60 mm) until one end of the stent made contact with the electrical connection at one end of the mandrel. This connection provides the ground potential to the stent. The motor may be activated and the stent rotated at a constant, slow speed. The syringe pump may then be activated to supply the nozzle with a consistent flow of solution, and the power supply may be activated to provide a charge to the solution and cause the solution to traverse the air gap and land on the stent surface. As the coated surfaces are rotated away from the spray path, the volatile portion of the solution evaporates leaving a coating of therapeutic agent behind. The stent continues to rotate in the spray pattern until the desired dose has been deposited on the abluminal surface. During the coating process, the stent is kept at ambient temperature and humidity, the solution is pumped at a rate of about 0.5-10 mL/hr, preferably about 0.5-8 mL/hr through the spray gun (which is placed at a horizontal distance of approximately 6 cm from the stents), and the bias voltage between the spray nozzle and the stent is approximately 5-20 kilovolts, preferably about 12 kilovolts. Substantially all of the solvent is evaporated during the spraying process, leaving a dose of about 0.1 micrograms-3 micrograms of paclitaxel per square millimeter on the abluminal surface area of the stent.

A layer of biodegradable polymer (e.g., PLA) may optionally be applied over the paclitaxel coating by dissolving approximately 1.2 g/L (±0.3 g/L) of PLA in a 2:1 v/v mixture of methanol and dichloromethane to obtain a finer spray that is more conducive to electrostatic spraying than the spray created by dissolving paclitaxel in dichloromethane alone. The solution is then applied to the stent by using an electrostatic spray deposition process as described above.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention. It is therefore intended that the foregoing detailed description be regarded as illustrative rather than limiting, and that it be understood that it is the following claims, including all equivalents, that are intended to define the spirit and scope of this invention.

We claim:

1. A method of coating a tubular medical device extending from a proximal end to a distal end along a longitudinal axis and having a plurality of openings between an abluminal surface and a luminal surface defining a substantially cylindrical lumen having a first diameter, the method comprising:

a. positioning the tubular medical device around a mandrel coating assembly having an axial member of a second diameter that is less than the first diameter of the lumen of the tubular medical device and at least one annular projection extending from the axial member to an outer surface, the annular projection configured to securably retain the tubular medical device around the axial member;

b. mounting the tubular medical device on the mandrel coating assembly with a first portion of the luminal surface contacting the annular projection, with at least a second portion of the luminal surface spaced apart from and substantially parallel to the axial member;

c. spraying a coating solution spray including a therapeutic agent and a solvent onto the abluminal surface of the tubular medical device mounted on the mandrel coating assembly to coat the abluminal surface of the medical device with the therapeutic agent while a portion of the coating solution spray passes through at least one opening in the medical device and terminates at the axial member without passing the axial member to directly contact the luminal surface of the medical device.

2. The method of claim 1, where the axial member is positioned along the longitudinal axis of the tubular medical device.

3. The method of claim 1, where the tubular medical device is a radially expandable vascular stent being movable from a radially compressed configuration to a radially expanded configuration.

4. The method of claim 3, where the tubular medical device is mounted on the mandrel coating assembly in a radially expanded state.

5. The method of claim 1, where the mandrel coating assembly includes a plurality of annular projections having an outer surface with an edge to minimize contact area of the luminal surface, the outer surface having an outer diameter at the edge substantially equal to the first diameter and extending from the axial member to contact the luminal surface.

6. The method of claim 1, where the mounted tubular medical device contacts one or more annular projections from the axial member without contacting the axial member.

7. The method of claim 1, where the axial member is rotated while spraying the coating solution.

8. The method of claim 1, where the spray is longitudinally translated relative to the medical device while spraying the coating solution.

9. The method of claim 1, where the solvent is an evaporative organic solvent.

10. The method of claim 1, where the therapeutic agent is paclitaxel.

11. The method of claim 1, where the coating solution further includes a polymer.

12. The method of claim 11, where the polymer is biodegradable.

13. A method of coating a tubular medical device extending along a longitudinal axis from a proximal end to a distal end and having a plurality of openings between an abluminal surface and a luminal surface defining a substantially cylindrical lumen having a first diameter, the method comprising:

a. positioning the tubular medical device around a mandrel coating assembly having a first axial member component and a second axial member component each having a second diameter that is less than the first diameter of the lumen of the tubular medical device, the first and second axial member components being removably coupled to one another, the first axial member component having a first annular projection and a means for coupling to the second axial member component, the second axial member component having a second annular projection and a means for coupling to the first axial member component, each of the first and second annular projections extending from the respective first and second axial member components to an outer surface having a diameter greater than the first diameter;

b. mounting the tubular medical device on the mandrel coating assembly having the first axial member component with the proximal end of the tubular medical device contacting the first annular projection, c. coupling the means for coupling of each of the first and second axial member components to one another, where the distal end of the tubular medical device contacts the second annular projection, the tubular medical device being secured to the mandrel coating assembly between the first and second annular projections with the luminal surface spaced apart from and substantially parallel to the first and second axial member components;

d. spraying a coating solution including a therapeutic agent and a solvent onto the abluminal surface of the tubular medical device mounted on the mandrel coating assembly as a coating solution spray to coat the abluminal surface of the tubular medical device with the therapeutic agent while a portion of the coating solution spray passes through at least one opening in the tubular medical device and terminates at the first and second axial member components without directly contacting the luminal surface of the tubular medical device.

14. The method of claim 13, where the first and second annular projections have an annular groove sized to receive the respective proximal and distal ends of the tubular medical device.

15. The method of claim 13, where the first and second axial member components are rotated while spraying the coating solution.

16. The method of claim 13, where the spray is longitudinally translated relative to the tubular medical device while spraying the coating solution.

17. The method of claim 13, where the solvent is an evaporative organic solvent and the method further comprises the step of evaporating the organic solvent to form a coating of the therapeutic agent on the abluminal surface of the tubular medical device.

18. A method of coating a tubular medical device extending along a longitudinal axis from a proximal end to a distal end and having a plurality of openings between an abluminal surface and a luminal surface defining a substantially cylindrical lumen having a first diameter, the method comprising:

a. positioning the tubular medical device around a mandrel coating assembly having an axial member of a second diameter that is less than the first diameter of the lumen of the tubular medical device and at least one support annular projection extending from the axial member to an outer surface having a diameter substantially equal to the first diameter to contact the luminal surface;

b. mounting the tubular medical device on the mandrel coating assembly with a first portion of the luminal surface contacting the outer surface of the at least one support annular projection, with at least a second portion of the luminal surface spaced apart from and substantially parallel to the axial member;

c. spraying a coating solution including a therapeutic agent and a solvent onto the abluminal surface of the mounted tubular medical device as a coating solution spray to coat the abluminal surface of the tubular medical device with the therapeutic agent while a portion of the coating solution spray passes through at least one opening in the tubular medical device, a spray pattern of the coating solution spray being configured to have a cross-sectional area that is smaller than the cross-sectional area of the axial member at the point of contact therebetween.

19. The method of claim 18, where the axial member further comprises a first spacing annular projection and a second spacing annular projection, each spacing annular projection extending from the axial member to an outer surface having a diameter greater than the first diameter and having an annular groove sized to receive one of the proximal and distal end of the tubular medical device, wherein the tubular medical device is positioned longitudinally between the first and second spacing annular projections.

20. The method of claim 18 where the axial member is rotated and the coating solution spray is longitudinally translated relative to the tubular medical device while spraying the coating solution.

* * * * *